United States Patent [19]

Taguchi et al.

[11] Patent Number: 5,036,086
[45] Date of Patent: Jul. 30, 1991

[54] NOVEL BENZOTHIAZOLE DERIVATIVES

[75] Inventors: Hiroaki Taguchi, Ibaraki; Takeo Katsushima, Kyoto; Masakazu Ban, Mukoh; Mitsuru Takahashi, Otsu; Kiyotaka Shinoda, Otsu; Akihiko Watanabe, Otsu, all of Japan

[73] Assignee: Toyo Boseki Kabushiki Kaisha, Osaka, Japan

[21] Appl. No.: 501,727

[22] Filed: Mar. 30, 1990

[30] Foreign Application Priority Data

May 11, 1989 [JP] Japan ................... 1-118146

[51] Int. Cl.$^5$ ................ C07D 277/82; A61K 31/425
[52] U.S. Cl. ..................... 514/367; 548/163
[58] Field of Search .................. 548/163; 514/367

[56] References Cited

U.S. PATENT DOCUMENTS 3,334,990  8/1967  Schäfer .......................... 71/88
4,791,112 12/1988  Bagley ........................... 514/252

Primary Examiner—Robert Gerstl
Attorney, Agent, or Firm—Wegner, Cantor, Mueller & Player

[57] ABSTRACT

Novel benzothiazole derivatives of the formula (I):

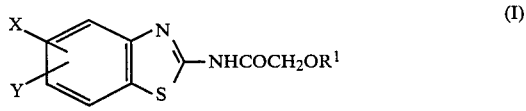

wherein $R^1$ is hydrogen atom, a lower alkyl group or a lower acyl group; X and Y are the same or different and are each hydrogen atom, a halogen atom, a lower alkyl group, a lower alkoxy group, nitro group, amino group, cyano group, trifluoromethyl group, a group of the formula: —$COOR^2$ (wherein $R^2$ is hydrogen atom, a lower alkyl group, an alkali metal, an alkaline earth metal, or a cation of amine), or a group of the formula: —$CONR^3R^4$ (wherein $R^3$ and $R^4$ are the same or different and are each hydrogen atom or a lower alkyl group) or a pharmaceutically acceptable acid addition salt thereof, which have excellent anti-allergic activity and are useful for the prophylaxis and treatment of various allergic diseases, and a pharmaceutical composition containing the compound as set forth above as an active ingredient.

4 Claims, No Drawings

NOVEL BENZOTHIAZOLE DERIVATIVES

This invention relates to novel benzothiazole derivatives having an anti-allergic activity and being useful as an anti-allergic agent. More particularly, it relates to benzothiazole derivatives of the general formula (I):

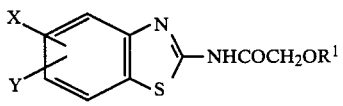

wherein $R^1$ is hydrogen atom, a lower alkyl group or a lower acyl group; X and Y are the same or different and are each hydrogen atom, a halogen atom, a lower alkyl group, a lower alkoxy group, nitro group, amino group, cyano group, trifluoromethyl group, a group of the formula: —$COOR^2$ (wherein $R^2$ is hydrogen atom, a lower alkyl group, an alkali metal, an alkaline earth metal, or a cation of amine), or a group of the formula: —$CONR^3R^4$ (wherein $R^3$ and $R^4$ are the same or different and are each hydrogen atom or a lower alkyl group), or a pharmaceutically acceptable acid addition salt thereof.

PRIOR ART

There have hitherto been studied various compounds useful for prophylaxis and treatment of various kinds of allergic symptoms and a number of such compounds have been reported. Known amide compounds having an anti-allergic activity are, for example, Tranilast [i.e. N-(3,4-dimethoxycinnamoyl)anthranilic acid] (cf. The Journal of Allergy and Clinical Immunology, Vol. 57, No. 5, page 396, 1976) and Lodoxamide Ethyl [i.e. diethyl N,N'-(2-chloro-5-cyano-m-phenylene)dioxamate] (cf. Agents and Actions, Vol. 1, page 235, 1975). However, known anti-allergic agents are not necessarily satisfactory for the treatment of various kinds of allergic diseases, particularly the treatment of bronchial asthma.

BRIEF DESCRIPTION OF THE INVENTION

The present inventors have intensively studied as to many kinds of compounds and the pharmacological activities thereof in order to find a compound having excellent anti-allergic activity and have found that some specific benzothiazole derivatives can show excellent anti-allergic activity.

An object of the invention is to provide novel benzothiazole derivatives having excellent anti-allergic activity against various kinds of allergic diseases. Another object of the invention is to provide a pharmaceutical composition containing said benzothiazole derivatives as an active ingredient which is useful for the prophylaxis and treatment of various allergic diseases. Another object of the invention is to provide a process for preparing the benzothiazole derivatives and a pharmaceutical composition thereof. These and other objects and advantages of the invention will be apparent to those skilled in the art from the following description.

DETAILED DESCRIPTION OF THE INVENTION

The benzothiazole derivatives of this invention are the compounds of the formula (I) as set forth hereinbefore.

In the formula (I), the lower alkyl group for $R^1$ denotes alkyl groups having 1 to 6 carbon atoms, including methyl, ethyl, n-propyl, n-butyl, n-pentyl, n-hexyl and an isomer thereof. Among them, methyl and ethyl groups are preferable. The lower acyl group for $R^1$ denotes acyl groups having 2 to 10 carbon atoms, including alkanoyl groups having 2 to 10 carbon atoms such as acetyl, propionyl, butyryl, isobutyryl, valeryl, isovaleryl, pivaloyl, hexanoyl, heptanoyl, octanoyl, nonanoyl, decanoyl; cycloalkylcarbonyl groups having 6 to 8 carbon atoms such as cyclopentylcarbonyl, cyclohexylcarbonyl; dibasic carboxyl groups having 2 to 4 cabon atoms such as oxalyl, malonyl, succinyl; benzoyl and a substituted benzoyl. Among them, acetyl, propionyl, butyryl, isobutyryl and benzoyl groups are preferable.

The halogen atom for X and Y includes fluorine, chlorine, bromine and iodine atoms, preferably fluorine and chlorine atoms. The lower alkyl group for X and Y includes alkyl groups having 1 to 6 carbon atoms, including methyl, ethyl, n-propyl, n-butyl, n-pentyl, n-hexyl and an isomer thereof. Among them, methyl and ethyl groups are preferable. The lower alkoxy group for X and Y denotes alkoxy groups having 1 to 6 carbon atoms, including methoxy, ethoxy, n-propoxy, n-butoxy, n-pentyloxy, n-hexyloxy and an isomer thereof. Preferable ones are methoxy and ethoxy groups.

The lower alkyl group for $R^2$ denotes alkyl groups having 1 to 6 carbon atoms, including methyl, ethyl, n-propyl, n-butyl, n-pentyl, n-hexyl and an isomer thereof. Among them, methyl and ethyl groups are preferable. The alkali metal for $R^2$ includes sodium and potassium and the alkaline earth metal for $R^2$ includes magnesium and calcium. The cation of amine for $R^2$ includes a cation of primary amine, secondary amine or tertiary amine, and a quarternary ammonium.

The lower alkyl group for $R^3$ and $R^4$ denotes alkyl groups having 1 to 6 carbon atoms, including methyl, ethyl, n-propyl, n-butyl, n-pentyl, n-hexyl and an isomer thereof. Among them, methyl and ethyl groups are preferable.

The compounds of the formula (I) wherein either one or both of X and Y are amino group can form an acid addition salt with a pharmaceutically acceptable acid, and this invention includes also such acid addition salts.

The acid addition salts include inorganic acid addition salts such as hydrochloride, hydrobromide, hydroiodide, sulfate, phosphate, nitrate and other ionic acid addition salts, and organic acid addition salts such as acetate, lactate, citrate, methanesulfonate, ethanesulfonate, benzenesulfonate, toluenesulfonate, isethionate and other ionic acid addition salts.

Preferred compounds of this invention are the benzothiazole derivatives of the formula (I) wherein $R^1$ is hydrogen atom, an alkyl group having 1 to 6 carbon atoms, an alkanoyl group having 2 to 6 carbon atoms, or benzoyl; X and Y are the same or different and are each hydrogen atom, a halogen atom, an alkyl group having 1 to 6 carbon atoms, an alkoxy group having 1 to 6 carbon atoms, nitro group, amino group, cyano group, trifluoro group, a group of the formula: —$COOR^2$ (wherein $R^2$ is hydrogen atom, an alkyl group having 1 to 6 carbon atoms, an alkali metal, an alkaline earth metal or a cation of amine) or a group of the formula: —$CONR^3R^4$ (wherein $R^3$ and $R^4$ are each hydrogen atom, or an alkyl group having 1 to 6 carbon atoms).

More preferred compounds of this invention are the benzothiazole derivatives of the formula (I) wherein $R^1$ is hydrogen atom, methyl group, ethyl group, acetyl group, propionyl group, butyryl group, isobutyryl group, or benzoyl group; X and Y are the same or different and are each hydrogen atom, fluorine atom, chlorine atom, methyl group, ethyl group, methoxy group, ethoxy group, nitro group, amino group, cyano group, trifluoromethyl group, a group of the formula: —COOR$^2$ (wherein R$^2$ is hydrogen atom, methyl group, ethyl group, sodium, potassium, calcium, a cation of primary amine, secondary amine, tertiary amine or a quarternary ammonium) or a group of the formula: —CONR$^3$R$^4$ (wherein R$^3$ and R$^4$ are each hydrogen atom, methyl group or ethyl group).

Particularly preferred compounds are the benzothiazole derivatives of the formula (I) wherein R$^1$ is hydrogen atom, methyl group, ethyl group, acetyl group, propionyl group, butyryl group, isobutyryl group, or benzoyl group; X and Y are the same or different and are each hydrogen atom, methyl group, methoxy group, ethoxy group, chlorine atom, fluorine atom, or nitro group.

Specifically preferred compounds are the following compounds:
2-(Methoxyacetylamino)benzothiazole
2-(Acetoxyacetylamino)-6-methoxybenzothiazole
2-(Hydroxyacetylamino)-6-methoxybenzothiazole
2-(Acetoxyacetylamino)-4-methoxybenzothiazole
2-(Hydroxyacetylamino)-4-methoxybenzothiazole
2-(Acetoxyacetylamino)-5,6-dimethylbenzothiazole
5,6-Dimethyl-2-(hydroxyacetylamino)benzothiazole
2-(Acetoxyacetylamino)-4-chlorobenzothiazole
4-Chloro-2-(hydroxyacetylamino)benzothiazole
6-Methoxy-2-(propionyloxyacetylamino)benzothiazole
2-(Butyryloxyacetylamino)-6-methoxybenzothiazole
2-(Isobutyryloxyacetylamino)-6-methoxybenzothiazole
2-(Benzoyloxyacetylamino)-6-methoxybenzothiazole
2-(Methoxyacetylamino)-4-methylbenzothiazole
2-(Methoxyacetylamino)-6-methylbenzothiazole
6-Ethoxy-2-(methoxyacetylamino)benzothiazole
2-(Methoxyacetylamino)-6-nitrobenzothiazole
2-(Ethoxyacetylamino)benzothiazole
6-Fluoro-2-(methoxyacetylamino)benzothiazole The benzothiazole derivatives (I) of this invention can be prepared, for example, by the following process, which comprises reacting an amino compound of the general formula (II):

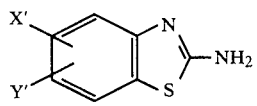

(II)

wherein X' and Y' are the same or different and are each hydrogen atom, a halogen atom, a lower alkyl group, a lower alkoxy group, nitro group, cyano group, trifluoromethyl group, a group of the formula: —COOR$^2$ (wherein R$^2$ is hydrogen atom or a lower alkyl group) or a group of the formula: —CONR$^3$R$^4$ (wherein R$^3$ and R$^4$ are the same different and are each hydrogen atom or a lower alkyl group), with an acid halide of the general formula (III):

R$^{1'}$OCH$_2$CO—Hal (III)

wherein R$^{1'}$ is a lower alkyl group or a lower acyl group, and Hal is a halogen atom, preferably chlorine atom.

The above reaction can be carried out in an appropriate solvent (e.g. pyridine, chloroform, diethyl ether, N,N-dimethylformamide, etc.) in the presence of a base (e.g. pyridine, triethylamine, etc.). The reaction proceeds without heating, but may be carried out with heating in order to ensure completion of the reaction. The reaction may also be carried out in the presence of an aqueous alkali solution like in Schotten Baumann reaction.

In case of the compounds of the formula (I) wherein R$^1$ is a lower acyl group, the obtained compounds may optionally be hydrolyzed to obtain the compounds of the formula (I) wherein R$^1$ is hydrogen atom.

The compounds of the formula (I) of this invention wherein R$^1$ is a lower acyl group can be prepared by reacting the compounds of the formula (I) of this invention wherein R$^1$ is hydrogen atom, with an acid halide of the general formula (IV):

R$^{1''}$—Hal (IV)

wherein R$^{1''}$ is a lower acyl group and Hal is as defined above or with an acid anhydride of the general formula (V):

R$^{1''}{}_2$O (V)

wherein R$^{1''}$ is as defined above.

The reaction between the compounds of the formula (I) wherein R$^1$ is hydrogen atom and the acid halide (IV) can be carried out in an appropriate solvent (e.g. pyridine, chloroform, diethyl ether, dichloromethane, N,N-dimethylformamide, etc.) in the presence of a base (e.g. pyridine, triethylamine, etc.). The reaction proceeds without heating, but may be carried out with heating in order to ensure completion of the reaction. The reaction may also be carried out in the presence of an aqueous alkali solution like in Schotten Baumann reaction.

The reaction between the compounds of the formula (I) wherein R$^1$ is hydrogen atom and the acid anhydride (V) can be carried out in a solvent (e.g. pyridine, chloroform, etc.) or without a solvent in the presence of a base (e.g. pyridine, triethylamine, etc.), an acid (e.g. sulfuric acid, etc.) or a catalyst (e.g. zinc chloride, etc.). The reaction proceeds without heating, but may be carried out with heating in order to ensure completion of the reaction.

In case of the compounds of the formula (I) wherein either one or both of X and Y are nitro group, the compounds may optionally be subjected to reduction to convert into the corresponding compounds (I) wherein either one or both of X and Y are amino group. Besides, the compounds of the formula (I) wherein either one or both of X and Y are amino group may optionally be converted into an acid addition salt thereof by treating them with an inorganic acid or organic acid in a usual manner.

In case of the compounds of the formula (I) wherein R$^2$ is a lower alkyl group, said alkyl group can be replaced with a different alkyl group by a conventional transesterification reaction. Besides, in case of the compounds of the formula (I) wherein R$^2$ is a lower alkyl group, the compounds may optionally be hydrolyzed to obtain the compounds of the formula (I) wherein R$^1$ is hydrogen atom.

In addition, the compounds of the formula (I) wherein R$^2$ is hydrogen atom can be converted into the compounds of the formula (I) wherein R$^2$ is an alkali metal, an alkaline earth metal or a cation of amine by a conventional procedure.

The compounds of this invention have potent inhibitory activity against immediate allergic reaction and hence are useful for the prophylaxis and treatment of immediate allergy, such as bronchial asthma, urticaria, allergic rhinitis, etc.

The compounds of this invention can be administered by oral or parenteral route, preferably by oral route. Alternatively, the compounds may be administered by inhalation in the form of aerosol spray or with an inhalator in the form of dry powder so that the compound can contact directly with the lung.

The clinical dose of the compounds of this invention may vary according to the kinds of the compounds, administration routes, severity of diseases, age, sex and body weight of patients, or the like, but is usually in the range of 2 to 2,000 mg per day in human. The dose may be divided and aministered in two to several times per day.

The compounds of this invention are usually administered to patients in the form of a pharmaceutical composition which contains a non-toxic and effective amount of the compounds. The pharmaceutical composition is in the dosage form of tablets, capsules, granules, syrups, powders, and the like for oral administration, and for the parenteral administration, they are in the form of aqueous solutions for intravenous injection, or oil suspension for intramuscular injection. The pharmaceutical composition is usually prepared by admixing the active compound of the formula (I) or a pharmaceutically acceptable acid addition salt thereof with conventional pharmaceutical carriers or diluents. Suitable examples of the carriers and diluents are lactose, glucose, dextrin, starch, sucrose, microcrystalline cellulose, sodium carboxymethylcellulose, calcium carboxymethylcellulose, gelatin, hydroxypropylcellulose, polyvinylpyrrolidone, magnesium stearate, talc, carboxyvinyl polymer, sorbitan fatty acid esters, sodium lauryl sulfate, macrogol, vegetable oils, wax, liquid paraffin, white petrolatum, propylene glycol, water, or the like.

This invention is illustrated by the following Examples and Experiment but should not be construed to be limited thereto.

EXAMPLE 1

Preparation of 2-(methoxyacetylamino)benzothiazole:

2-Aminobenzothiazole (4.5 g) is dissolved in pyridine (100 ml) and thereto is added dropwise methoxyacetyl chloride (3.0 ml) at room temperature. After the mixture is stirred at room temperature for 2 hours, the solvent is distilled off. The resulting oil is dissolved in chloroform and the organic layer is washed with water and then with a saturated saline. The organic layer is dried over anhydrous sodium sulfate and the solvent is distilled off. The resulting solids are recrystallized from ethanol/water to give the title compound (5.2 g) having the following physical properties.

Melting point: 99°–100° C.

IR (KBr) $v$: 3460, 3180, 3000, 2940, 2900, 2820, 1685, 1600, 1555, 1535, 1470, 1455, 1445, 1420, 1350, 1270, 1195, 1120, 925, 780, 760, 750 cm$^{-1}$

NMR (DMSO-d$_6$) $\delta$: 11.20 (1H, br.s), 8.10–7.12 (4H), 4.18 (2H, s), 3.36 (1H, s)

Elementary analysis:
Calcd. (%): C,54.04; H,4.53; N,12.60; S,14.27;
Found (%): C,54.29; H,4.48; N,12.59; S,14.42.

EXAMPLE 2

Preparation of 2-(acetoxyacetylamino)-6-methoxybenzothiazole:

2-Amino-6-methoxybenzothiazole (12.0 g) is dissolved in pyridine (250 ml) and thereto is added dropwise acetoxyacetyl chloride (7.9 ml) at room temperature. After the mixture is stirred at room temperature for 2 hours, the solvent is distilled off. The resulting solids are washed with water and then with diethyl ether, dried and recrystallized from ethanol to give the title compound (15.3 g) having the following physical properties.

Melting point: 196°–197° C.

IR (KBr) $v$: 3450, 3230, 1725, 1700, 1605, 1570, 1560, 1470, 1435, 1300, 1280, 1265, 1255, 1230, 1055, 1025, 980, 840 cm$^{-1}$.

NMR (DMSO-d$_6$) $\delta$: 12.35 (1H, br.s), 7.58 (1H, d), 7.51 (1H, d), 6.99 (1H, d of d), 4.74 (2H, s), 3.74 (3H, s), 2.08 (3H, s).

Elementary analysis:
Calcd. (%): C,51.42; H,4.31; N,9.99; S,11.44;
Found (%): C,51.48; H,4.37; N,10.01; S,11.45.

EXAMPLE 3

Preparation of 2-(hydroxyacetylamino)-6-methoxybenzothiazole:

2-(Acetoxyacetylamino)-6-methoxybenzothiazole (13.0 g) prepared in Example 2 is dissolved in methanol (1000 ml) and thereto is added 28% aqueous ammonia (100 ml) and the mixture is stirred at room temperature for 1 hour. The solvent is distilled off and the resulting solids are washed with water, dried and recrystallized from ethanol to give the title compound (10.3 g) having the following physical properties.

Melting point: 208°–209° C.

IR (KBr) $v$: 3470, 3240, 1690, 1615, 1570, 1475, 1300, 1280, 1230, 1110, 1070, 1040, 975, 870, 805 cm$^{-1}$.

NMR (DMSO-d$_6$) $\delta$: 11.25 (1H, br.s), 7.60 (1H, d), 7.54 (1H, d), 6.99 (1H, d of d), 5.51 (1H, br.s), 4.18 (2H, s), 3.80 (3H, s).

Elementary analysis:
Calcd. (%): C,50.41; H,4.23; N,11.76;
Found (%): C,50.52; H,4.33; N,11.70.

EXAMPLE 4

Preparation of 2-(acetoxyacetylamino)-4-methoxybenzothiazole:

2-Amino-4-methoxybenzothiazole (4.5 g) is dissolved in pyridine (80 ml) and thereto is added dropwise acetoxyacetyl chloride (3.0 ml) at room temperature. After the mixture is stirred at room temperature for 2 hours, the solvent is distilled off. The resulting solids are washed with water and then with diethyl ether, dried and recrystallized from ethanol to give the title compound (4.3 g) having the following physical properties.

Melting point: 161°–162° C.

IR (KBr) $v$: 3460, 2940, 1745, 1715, 1600, 1555, 1480, 1425, 1315, 1275, 1205, 1080, 1045, 975, 775, 745 cm$^{-1}$.

NMR (DMSO-d$_6$) $\delta$: 12.63 (1H, br.s), 7.61–6.83 (3H), 4.80 (2H, s), 3.90 (3H, s), 2.15 (3H, s).

Elementary analysis:
Calcd. (%): C,51.42; H,4.31; N,9.99;
Found (%): C,51.22; H,4.37; N,9.97.

EXAMPLE 5

Preparation of 2-(hydroxyacetylamino)-4-methoxybenzothiazole:

2-(Acetoxyacetylamino)-4-methoxybenzothiazole (1.0 g) prepared in Example 4 is dissolved in methanol (40 ml) and thereto is added 28% aqueous ammonia (4 ml) and the mixture is stirred at room temperature for 1 hour. The solvent is distilled off and the resulting solids are washed with water, dried and recrystallized from ethanol to give the title compound (0.7 g) having the following physical properties.

Melting point: 193°–195° C.

IR (KBr) $\nu$: 3390, 2930, 1710, 1605, 1580, 1550, 1485, 1430, 1350, 1290, 1280, 1270, 1210, 1085, 1045, 985, 775, 740 cm$^{-1}$.

NMR (DMSO-$d_6$) $\delta$: 12.02 (1H, br.s), 7.56–6.80 (3H), 5.50 (1H, t), 4.15 (2H, d), 3.90 (3H, s).

Elementary analysis:
Calcd. (%): C,50.41; H,4.23; N,11.76; S,13.46;
Found (%): C,50.35; H,4.27; N,11.73; S,13.51.

EXAMPLE 6

Preparation of 2-(acetoxyacetylamino)-5,6-dimethylbenzothiazole:

2-Amino-5,6-dimethylbenzothiazole (4.5 g) is dissolved in pyridine (80 ml) and thereto is added dropwise acetoxyacetyl chloride (3.0 ml) at room temperature. After the mixture is stirred at room temperature for 2 hours, the solvent is distilled off. The resulting oil is solidified with addition of water. The obtained solids are filtered off and washed with water, then with diethyl ether, dried and recrystallized from ethanol to give the title compound (5.4 g) having the following physical properties.

Melting point: 214°–215° C.

IR (KBr) $\nu$: 3470, 3160, 2930, 1760, 1740, 1570, 1555, 1460, 1290, 1240, 1180, 1095, 1045, 970, 860 cm$^{-1}$.

NMR (DMSO-$d_6$) $\delta$: 12.39 (1H, br.s), 7.67 (1H, s), 7.51 (1H, s), 4.78 (2H, s), 2.30 (6H, s), 2.13 (3H, s).

Elementary analysis:
Calcd. (%): C,56.10; H,5.07; N,10.06; S,11.52;
Found (%): C,56.06; H,5.07; N,10.06; S,11.43.

EXAMPLE 7

Preparation of 5,6-dimethyl-2-(hydroxyacetylamino)benzothiazole:

2-(Acetoxyacetylamino)-5,6-dimethylbenzothiazole (4.2 g) prepared in Example 6 is dissolved in methanol (200 ml) and thereto is added 28% aqueous ammonia (20 ml) and the mixture is stirred at room temperature for 1 hour. The solvent is distilled off and the resulting solids are washed with water, dried and recrystallized from ethanol to give the title compound (3.2 g) having the following physical properties.

Melting point: 206°–208° C.

IR (KBr) $\nu$: 3380, 1720, 1620, 1570, 1540, 1480, 1470, 1445, 1410, 1400, 1290, 1080, 970, 885, 855 cm$^{-1}$.

NMR (DMSO-$d_6$) $\delta$: 11.28 (1H, br.s), 7.66 (1H, s), 7.49 (1H, s), 5.49 (1H, t), 4.13 (2H, d), 2.31 (6H, s).

Elementary analysis:
Calcd. (%): C,55.92; H,5.12; N,11.86; S,13.57;
Found (%): C,55.82; H,5.19; N,11.79; S,13.50.

EXAMPLE 8

Preparation of 2-(acetoxyacetylamino)-4-chlorobenzothiazole:

2-Amino-4-chlorobenzothiazole (4.6 g) is dissolved in pyridine (80 ml) and thereto is added dropwise acetoxyacetyl chloride (3.0 ml) at room temperature. After the mixture is stirred at room temperature for 2 hours, the solvent is distilled off. The resulting solids are washed with water, then with diethyl ether, dried and recrystallized from ethanol to give the title compound (4.6 g) having the following physical properties.

Melting point: 205°–207° C.

IR (KBr) $\nu$: 3470, 3230, 1730, 1705, 1600, 1515, 1440, 1420, 1400, 1380, 1320, 1310, 1285, 1255, 1195, 1115, 1015, 1070, 985, 875, 830, 775, 745 cm$^{-1}$.

NMR (DMSO-$d_6$) $\delta$: 12.90 (1H, br.s), 8.00–7.17 (3H), 4.82 (2H, s), 2.15 (3H, s).

Elementary analysis:
Calcd. (%): C,46.40; H,3.19; N,9.84; S,11.26; Cl,12.45;
Found (%): C,46.29; H,3.22; N,9.82; S,11.30; Cl,12.44.

EXAMPLE 9

Preparation of 4-chloro-2-(hydroxyacetylamino)benzothiazole:

2-(Acetoxyacetylamino)-4-chlorobenzothiazole (2.8 g) prepared in Example 8 is dissolved in methanol (100 ml) and thereto is added 28% aqueous ammonia (10 ml) and the mixture is stirred at room temperature for 1 hour. The solvent is distilled off and the resulting solids are washed with water, dried and recrystallized from ethanol to give the title compound (1.9 g) having the following physical properties.

Melting point: 242°–245° C.

IR (KBr) $\nu$: 3360, 1720, 1600, 1555, 1425, 1325, 1295, 1290, 1180, 1115, 1080, 995, 880, 830, 770, 740 cm$^{-1}$.

NMR (DMSO-$d_6$) $\delta$: 12.40 (1H, br.s), 8.05–7.16 (3H), 5.47 (1H, t), 4.20 (2H, d).

Elementary analysis:
Calcd. (%): C,44.54; H,2.91; N,11.54; Cl,14.61;
Found (%): C,44.54; H,3.01; N,11.46; Cl,14.65.

EXAMPLE 10

Preparation of 6-methoxy-2-(propionyloxyacetylamino)benzothiazole:

2-(Hydroxyacetylamino)-6-methoxybenzothiazole (1.2 g) prepared in Example 3 is dissolved in pyridine (50 ml) and thereto is added dropwise propionyl chloride (0.5 ml) at room temperature. After the mixture is stirred at room temperature for 2 hours, the solvent is distilled off. The resulting oil is solidified with addition of water. The obtained solids are filtered off and washed with water, then with diethyl ether, dried and recrystallized from ethanol to give the title compound (1.1 g) having the following physical properties.

Melting point: 145°–147° C.

IR (KBr) $\nu$: 3350, 2960, 1720, 1705, 1615, 1575, 1565, 1475, 1445, 1305, 1265, 1235, 1180, 1100, 1065, 1035, 980, 840, 820 cm$^{-1}$.

NMR (DMSO-$d_6$) $\delta$: 12.35 (1H, br.s), 7.73–6.86 (3H), 4.79 (2H, s), 3.77 (3H, s), 2.44 (2H, q), 1.08 (3H, t).

Elementary analysis:
Calcd. (%): C,53.05; H,4.79; N,9.52; S,10.89;
Found (%): C,53.15; H,4.80; N,9.49; S,10.86.

EXAMPLE 11

Preparation of 2-(butyryloxyacetylamino)-6-methoxybenzothiazole:

2-(Hydroxyacetylamino)-6-methoxybenzothiazole (1.2 g) prepared in Example 3 is dissolved in pyridine (50 ml) and thereto is added dropwise butyryl chloride (0.6 ml) at room temperature. After the mixture is stirred at room temperature for 2 hours, the solvent is distilled off.

The resulting oil is solidified with addition of water. The obtained solids are filtered off, washed with water, then with diethyl ether, dried and recrystallized from ethanol to give the title compound (1.2 g) having the following physical properties.

Melting point: 152°–153° C.

IR (KBr) ν: 3450, 3270, 2970, 1725, 1710, 1610, 1575, 1565, 1475, 1440, 1325, 1290, 1265, 1235, 1175, 1060, 1030, 980, 840, 830 cm$^{-1}$

NMR (DMSO-d$_6$) δ: 12.36 (1H, br.s), 7.70–6.84 (3H), 4.79 (2H, s), 3.78 (3H, s), 2.40 (2H, t), 1.60 (2H, d of t), 0.93 (3H, t)

Elementary analysis:
Calcd. (%): C,54.53; H,5.23; N,9.08; S,10.40;
Found (%): C,54.55; H,5.27; N,9.17; S,10.50.

EXAMPLE 12

Preparation of 2-(isobutyryloxyacetylamino)-6-methoxybenzothiazole:

2-(Hydroxyacetylamino)-6-methoxybenzothiazole (1.2 g) prepared in Example 3 is dissolved in pyridine (50 ml) and thereto is added dropwise isobutyryl chloride (0.6 ml) at room temperature. After the mixture is stirred at room temperature for 2 hours, the solvent is distilled off. The resulting oil is solidified with addition of water. The obtained solids are filtered off, washed with water, then with diethyl ether, dried and recrystallized from ethanol to give the title compound (1.2 g) having the following physical properties.

Melting point: 141°–142° C.

IR (KBr) ν: 3460, 3270, 2990, 1745, 1705, 1610, 1565, 1475, 1440, 1270, 1260, 1150, 1060, 1030, 980, 825 cm$^{-1}$.

NMR (DMSO-d$_6$) δ: 12.36 (1H, br.s), 7.72–6.90 (3H), 4.80 (2H, s), 3.78 (3H, s), 2.62 (1H, q), 1.15 (6H, d).

Elementary analysis:
Calcd. (%): C,54.53; H,5.23; N,9.08; S,10,40
Found (%): C,54.41; H,5.27; N,9.14; S,10.50

EXAMPLE 13

Preparation of 2-(benzoyloxyacetylamino)-6-methoxybenzothiazole:

2-(Hydroxyacetylamino)-6-methoxybenzothiazole (1.2 g) prepared in Example 3 is dissolved in pyridine (50 ml) and thereto is added dropwise benzoyl chloride (0.6 ml) at room temperature. After the mixture is stirred at room temperature for 2 hours, the solvent is distilled off. The resulting oil is solidified with addition of water. The obtained solids are filtered off, washed with water, then with diethyl ether, dried and recrystallized from ethanol to give the title compound (1.3 g) having the following physical properties.

Melting point: 203°–204° C.

IR (KBr) ν: 3460, 3270, 1705, 1610, 1580, 1560, 1480, 1440, 1300, 1270, 1185, 1135, 1065, 1035, 980, 835, 720 cm$^{-1}$.

NMR (DMSO-d$_6$) δ: 12.51 (1H, br.s), 8.16–6.85 (8H), 5.07 (2H, s), 3.78 (3H, s).

Elementary analysis:
Calcd. (%): C,59.64; H,4.12; N,8.18; S,9.36;
Found (%): C,59.45; H,4.04; N,8.15; S,9.41.

EXAMPLE 14

Preparation of 2-(methoxyacetylamino)-4-methylbenzothiazole:

2-Amino-4-methylbenzothiazole (4.9 g) is dissolved in pyridine (100 ml) and thereto is added dropwise methoxyacetyl chloride (3.0 ml) at room temperature. After the mixture is stirred at room temperature for 2 hours, the solvent is distilled off. The resulting oil is solidified with addition of water. The obtained solids are filtered off and washed with water, then with diethyl ether, dried and recrystallized from ethanol to give the title compound (5.2 g) having the following physical properties.

Melting point: 110°–111° C.

IR (KBr) ν: 3470, 3270, 1705, 1590, 1540, 1460, 1410, 1290, 1270, 1200, 1120, 995, 980, 865, 765, 755 cm$^{-1}$.

NMR (DMSO-d$_6$) δ: 12.23 (1H, br.s), 7.86–7.53 (1H), 7.30–7.10 (2H), 4.20 (2H, s), 3.55 (3H, s), 2.12 (3H, s).

Elementary analysis:
Calcd. (%): C,55.92; H,5.12; N,11.86; S,13.57;
Found (%): C,55.74; H,5.22; N,11.92; S,13.58.

EXAMPLE 15

Preparation of 2-(methoxyacetylamino)-6-methylbenzothiazole:

2-Amino-6-methylbenzothiazole (4.9 g) is dissolved in pyridine (100 ml) and thereto is added dropwise methoxyacetyl chloride (3.0 ml) at room temperature. After the mixture is stirred at room temperature for 2 hours, the solvent is distilled off. The resulting oil is solidified with addition of water. The obtained solids are filtered off and washed with water, then with diethyl ether, dried and recrystallized from ethanol to give the title compound (4.1 g) having the following physical properties.

Melting point: 134°–135° C.

IR (KBr) ν: 3470, 3180, 3070, 2980, 2920, 1730, 1610, 1545, 1465, 1275, 1205, 1185, 1130, 1070, 980, 935, 810 cm$^{-1}$.

NMR (DMSO-d$_6$) δ: 12.10 (1H, br.s), 7.77–7.44 (2H), 7.32–7.06 (1H), 4.17 (2H, s), 3.36 (3H, s), 2.38 (3H, s).

Elementary analysis:
Calcd. (%): C,55.92; H,5.12; N,11.86; S,13.57;
Found (%): C,55.78; H,5.18; N,11.80; S,13.60.

EXAMPLE 16

Preparation of 6-ethoxy-2-(methoxyacetylamino)benzothiazole:

2-Amino-6-ethoxybenzothiazole (5.8 g) is dissolved in pyridine (100 ml) and thereto is added dropwise methoxyacetyl chloride (3.0 ml) at room temperature. After the mixture is stirred at room temperature for 2 hours, the solvent is distilled off. The resulting solids are washed with water, then with diethyl ether, dried and recrystallized from ethanol to give the title compound (5.1 g) having the following physical properties.

Melting point: 144°–145° C.

IR (KBr) ν: 3480, 3200, 3080, 3000, 2940, 1705, 1610, 1570, 1545, 1470, 1400, 1300, 1275, 1235, 1125, 1065, 1045, 945, 900, 825 cm$^{-1}$.

NMR (DMSO-d$_6$) δ: 12.01 (1H, br.s), 7.12 (1H, d), 7.01 (1H, d), 6.92 (1H, d of d), 4.19 (2H, s), 4.01 (2H, q), 3.38 (3H, s), 1.36 (3H, t).

Elementary analysis
Calcd. (%): C,54.12; H,5.30; N,10.52; S,12.04;
Found (%) C,54.29; H,5.35; N,10.55; S,12.09.

EXAMPLE 17

Preparation of 2-(methoxyacetylamino)-6-nitrobenzothiazole:

2-Amino-6-nitrobenzothiazole (5.9 g) is dissolved in pyridine (100 ml) and thereto is added dropwise methoxyacetyl chloride (3.0 ml) at room temperature. After the mixture is stirred at room temperature for 2 hours, the solvent is distilled off. The resulting solids are washed with water, then with diethyl ether, dried and recrystallized from ethanol to give the title compound (5.1 g) having the following physical properties.
Melting point: 230°-233° C.
IR (KBr) ν: 3475, 3310, 1705, 1580, 1540, 1455, 1355, 1285, 1200, 1120, 1050, 940, 910, 900, 840, 760 cm$^{-1}$.
NMR (DMSO-d$_6$) δ: 12.64 (1H, br.s), 9.01 (1H, d), 8.25 (1H, d of d), 7.85 (1H, d), 4.24 (2H, s), 3.39 (3H, q).
Elementary analysis:
Calcd. (%): C,44.94; H,3.39; N,15.72; S,12.00;
Found (%): C,44.80; H,3.46; N,15.78; S,12.04.

EXAMPLE 18

Preparation of 2-(ethoxyacetylamino)benzothiazole:
2-Aminobenzothiazole (4.5 g) is dissolved in pyridine (100 ml) and thereto is added dropwise ethoxyacetyl chloride (3.0 ml) at room temperature. After the mixture is stirred at room temperature for 2 hours, the solvent is distilled off. The resulting solids are washed with water, dried and recrystallized from a mixed solvent of diethyl ether/n-hexane to give the title compound (4.5 g) having the following physical properties.
Melting point: 113°-114° C.
IR (KBr) ν: 3475, 2990, 2900, 1705, 1685, 1605, 1550, 1540, 1450, 1285, 1135, 1125, 1045, 1020, 900, 765 cm$^{-1}$.
NMR (DMSO-d$_6$) δ: 12.20 (1H, br.s), 8.17-7.22 (4H), 4.28 (2H, s), 3.62 (2H, q), 1.25 (3H, t).
Elementary analysis:
Calcd. (%): C,55.92; H,5.12; N,11.86; S,13.57;
Found (%): C,55.88; H,5.20; N,11.81; S,13.60.

EXAMPLE 19

Preparation of 6-fluoro-2-(methoxyacetylamino)benzothiazole:
2-Amino-6-fluorobenzothiazole (3.3 g) is dissolved in pyridine (80 ml) and thereto is added dropwise methoxyacetyl chloride (2.0 ml) at room temperature. After the mixture is stirred at room temperature for 2 hours, the solvent is distilled off. The resulting solids are washed with water, then with diethyl ether, dried and recrystallized from ethanol to give the title compound (3.5 g) having the following physical properties.
Melting point: 139°-140° C.
IR (KBr) ν: 3140, 2980, 1900, 1720, 1605, 1560, 1540, 1460, 1415, 1275, 1255, 1205, 1175, 1120, 1050, 970, 925, 870, 805 cm$^{-1}$.
NMR (DMSO-d$_6$) δ: 12.21 (1H, br.s), 8.02-7.54 (2H), 7.46-7.07 (1H), 4.18 (2H, s), 3.36 (3H, s).
Elementary analysis:
Calcd. (%): C,49.99; H,3.78; N,11.66; S,13.34; F,7.91;
Found (%): C,49.90; H,3.83; N,11.70; S,13.28; F,7.80.

The anti-allergic activity of the compounds of this invention is illustrated by the following experiment.

Experiment

Male Wistar rats (weighing about 200 g) were passively sensitized by intradermal injection of each 0.1 ml of a solution of rat antiserum to egg albumin in each two sites (totally four sites) at both sides of dorsal median line. After 48 hours, each rat was challenged by injecting a mixture (1 ml) of egg albumin and Evans blue solution via tail vein to induce passive cutaneous anaphylaxis (PCA). Thirty minutes after the challenge, the rats were sacrificed to take the blueing region, and the amount of pigment from the blueing region was measured by the method of Katayama et al. (cf. Microbiol. Immunol., Vol. 22, page 89, 1978). Test compounds were orally administered to the rats (each 3 rats) in a dose of 30 mg/kg 30 minutes before the antigen challenge. The PCA inhibitory rate of the compounds of this invention is shown in Table 1.

TABLE 1

| Test compounds | PCA inhibitory rate (%) |
| --- | --- |
| 2-(Methoxyacetylamino)benzothiazole (compound in Example 1) | 96 |
| 2-(Acetoxyacetylamino)-6-methoxy-benzothiazole (compound in Example 2) | 96 |
| 2-(Hydroxyacetylamino)-6-methoxy-benzothiazole (compound in Example 3) | 90 |
| 2-(Acetoxyacetylamino)-4-methoxy-benzothiazole (compound in Example 4) | 85 |
| 2-(Hydroxyacetylamino)-4-methoxy-benzothiazole (compound in Example 5) | 82 |
| 2-(Acetoxyacetylamino)-5,6-dimethyl-benzothiazole (compound in Example 6) | 84 |
| 5,6-Dimethyl-2-(hydroxyacetylamino)-benzothiazole (compound in Example 7) | 80 |
| 2-(Acetoxyacetylamino)-4-chloro-benzothiazole (compound in Example 8) | 90 |
| 4-Chloro-2-(hydroxyacetylamino)-benzothiazole (compound in Example 9) | 90 |
| 6-Methoxy-2-(propionyloxyacetylamino)-benzothiazole (compound in Example 10) | 92 |
| 2-(Butyryloxyacetylamino)-6-methoxy-benzothiazole (compound in Example 11) | 93 |
| 2-(Isobutyryloxyacetylamino)-6-methoxy-benzothiazole (compound in Example 12) | 92 |
| 2-(Benzoyloxyacetylamino)-6-methoxy-benzothiazole (compound in Example 13) | 73 |
| 2-(Methoxyacetylamino)-4-methyl-benzothiazole (compound in Example 14) | 95 |
| 2-(Methoxyacetylamino)-6-methyl-benzothiazole (compound in Example 15) | 92 |
| 6-Ethoxy-2-(methoxyacetylamino)-benzothiazole (compound in Example 16) | 88 |
| 2-(Methoxyacetylamino)-6-nitro-benzothiazole (compound in Example 17) | 80 |
| 2-(Ethoxyacetylamino)benzothiazole (compound in Example 18) | 71 |
| 6-Fluoro-2-(methoxyacetylamino)-benzothiazole (compound in Example 19) | 95 |

What is claimed is:
1. A benzothiazole derivative of the formula (I):

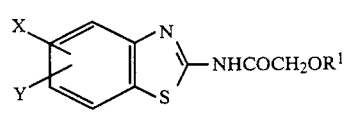

wherein R$^1$ is hydrogen atom, or an acyl group selected from the group consisting of an alkanoyl group having 2 to 10 carbon atoms, a cycloalkylcarbonyl group having 6 to 8 carbon atoms, a dibasic carboxyl group having 2 to 4 carbon atoms and benzoyl; X and Y are the same or different and are each hydrogen atom, a halogen atom, an alkyl group having 1 to 6 carbon atoms, an alkoxy group having 1 to 6 carbon atoms, nitro group, amino group, cyano group, trifluoromethyl group, a group of the formula: —COOR$^2$ (wherein R$^2$ is hydrogen atom, an alkyl group having 1 to 6 carbon atoms, an alkali metal, an alkaline earth metal, or a cation of amine), or a group of the formula: —CONR$^3$R$^4$ (wherein R$^3$ and R$^4$ are the same or different and are each hydrogen atom or an alkyl group having 1 to 6 carbon atoms), or a pharmaceutically acceptable acid addition salt thereof.

2. The compound according to claim 1 which is a member selected from the following compounds:

2-(Acetoxyacetylamino)-6-methoxybenzothiazole
2-(Hydroxyacetylamino)-6-methoxybenzothiazole
2-(Acetoxyacetylamino)-4-methoxybenzothiazole
2-(Hydroxyacetylamino)-4-methoxybenzothiazole
2-(Acetoxyacetylamino)-5,6-dimethylbenzothiazole
5,6-Dimethyl-2-(hydroxyacetylamino)benzothiazole
2-(Acetoxyacetylamino)-4-chlorobenzothiazole
4-Chloro-2-(hydroxyacetylamino)benzothiazole
6-Methoxy-2-(propionyloxyacetylamino)benzothiazole
2-(Butyryloxyacetylamino)-6-methoxybenzothiazole
2-(Isobutyryloxyacetylamino)-6-methoxybenzothiazole
2-(Benzoyloxyacetylamino)-6-methoxybenzothiazole.

3. A method for the prophylaxis and treatment of immediate allergic reaction, which comprises administering to a patient in need thereof a prophylactically or therapeutically effective amount of a compound of the formula

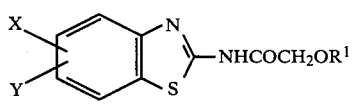

(I)

wherein $R^1$ is hydrogen atom, an alkyl group having 1 to 6 carbon atoms or an acyl group selected from the group consisting of an alkanoyl group having 2 to 10 carbon atoms, a cycloalkylcarbonyl group having 6 to 8 carbon atoms, a dibasic carboxyl group having 2 to 4 carbon atoms and benzoyl; X and Y are the same or different and are each hydrogen atom, a halogen atom, an alkyl group having 1 to 6 carbon atoms, an alkoxy group having 1 to 6 carbon atoms, nitro group, amino group, cyano group, trifluoromethyl group, a group of the formula —COOR$^2$ (wherein $R^2$ is hydrogen atom, an alkyl group having 1 to 6 carbon atoms, an alkali metal, an alkaline earth metal, or a cation of amine) or a group of the formula —CONR$^3$R$^4$ (wherein $R^3$ and $R^4$ are each hydrogen atom or an alkyl group having 1 to 6 carbon atoms), or a pharmaceutically acceptable acid addition salt thereof.

4. A method according to claim 3, wherein the compound is selected from:
2-(Acetoxyacetylamino)-6-methoxybenzothiazole
2-(Hydroxyacetylamino)-6-methoxybenzothiazole
2-(Acetoxyacetylamino)-4-methoxybenzothiazole
2-(Hydroxyacetylamino)-4-methoxybenzothiazole
2-(Acetoxyacetylamino)-5,6-dimethylbenzothiazole
5,6-Dimethyl-2-(hydroxyacetylamino)benzothiazole
2-(Acetoxyacetylamino)-4-chlorobenzothiazole
4-Chloro-2-(hydroxyacetylamino)benzothiazole
6-Methoxy-2-(propionyloxyacetylamino)benzothiazole
2-(Butyryloxyacetylamino)-6-methoxybenzothiazole
2-(Isobutyryloxyacetylamino)-6-methoxybenzothiazole
2-(Benzoyloxyacetylamino)-6-methoxybenzothiazole
2-(Methoxyacetylamino)-4-methylbenzothiazole
2-(Methoxyacetylamino)-6-methylbenzothiazole
6-Ethoxy-2-(methoxyacetylamino)benzothiazole
2-(Methoxyacetylamino)-6-nitrobenzothiazole
2-(Ethoxyacetylamino)benzothiazole and
6-Fluoro-2-(methoxyacetylamino)benzothiazole.

* * * * *